United States Patent
Sugita et al.

(10) Patent No.: US 6,416,544 B2
(45) Date of Patent: *Jul. 9, 2002

(54) STENT MANUFACTURING METHOD THEREOF AND INDWELLING METHOD THEREOF

(75) Inventors: Yoichi Sugita, Tokyo; Akira Ogawa; Kenji Kyo, both of Kasukabe, all of (JP)

(73) Assignee: Actment Co., Ltd., Saitama-Ken (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/437,606

(22) Filed: Nov. 10, 1999

(30) Foreign Application Priority Data

Nov. 11, 1998 (JP) ............................................. 10-321102

(51) Int. Cl.⁷ .................................................. A61F 2/06
(52) U.S. Cl. ...................................................... 623/1.19
(58) Field of Search ................................. 623/1.15, 900, 623/1, 1.11, 1.12, 1.13, 1.18, 1.19, 1.2, 1.22; 606/191, 108, 198, 194; 148/402

(56) References Cited

U.S. PATENT DOCUMENTS

| | | | | |
|---|---|---|---|---|
| 4,586,969 A | * | 5/1986 | Tamura et al. | |
| 5,292,331 A | * | 3/1994 | Boneau | 623/1 |
| 5,624,508 A | * | 4/1997 | Flomenblit et al. | 148/510 |
| 5,645,559 A | * | 7/1997 | Hachman et al. | 606/198 |
| 5,716,410 A | * | 2/1998 | Wang et al. | 606/191 |
| 5,976,152 A | * | 11/1999 | Regan et al. | 606/191 |
| 5,980,566 A | * | 11/1999 | Alt et al. | 623/1 |
| 6,083,257 A | * | 7/2000 | Taylor et al. | 623/1 |

FOREIGN PATENT DOCUMENTS

| | | |
|---|---|---|
| EP | 0 411 118 | 10/1988 |
| JP | 3-51430 | 8/1991 |

OTHER PUBLICATIONS (1) English Language Abstract of JP 3–51430.

* cited by examiner

Primary Examiner—Michael J. Milano
Assistant Examiner—Vy Q. Bui
(74) Attorney, Agent, or Firm—Lowe Hauptman Gilman & Berman LLP

(57) ABSTRACT

A stent is reversibly deformable between a lower-temperature shape and a higher-temperature shape in accordance with temperature changes in a patient's body. The stent has a hollow cylindrical body formed by a plurality of braided filament bodies made of a Ti—Ni alloy of excessive Ni. A lower-temperature shape memorizing process and a higher-temperature shape memorizing process are conducted to the hollow cylindrical body to memorize the lower-temperature and higher-temperature shapes, respectively. The crossing filament bodies are fixed only at the ends of the stent.

10 Claims, 11 Drawing Sheets

FIG. 12
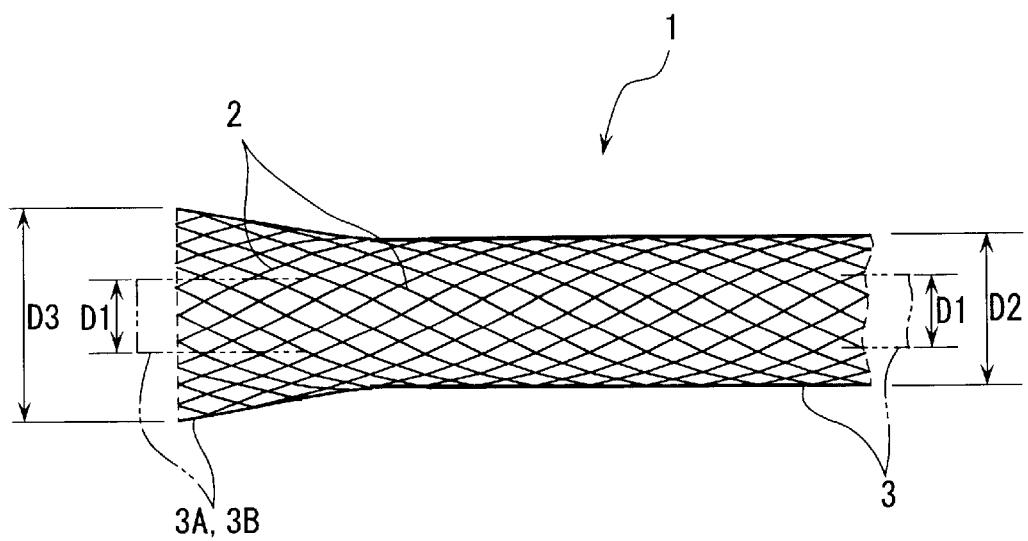
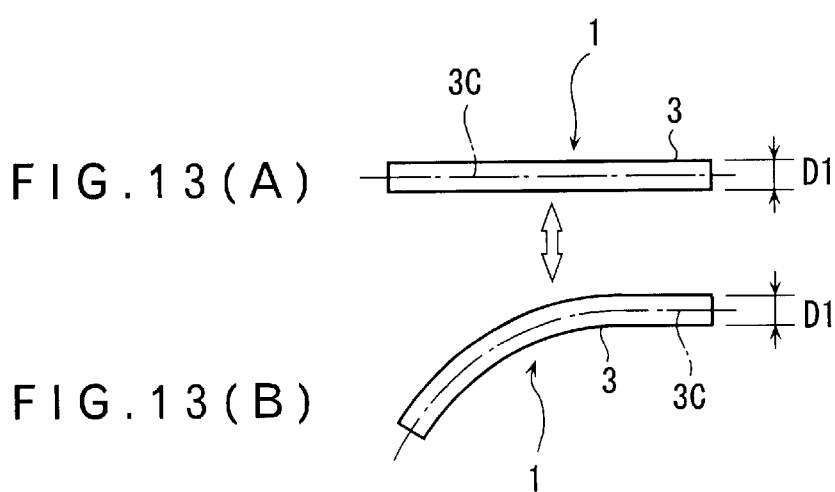
FIG. 13(A)
FIG. 13(B)

STENT MANUFACTURING METHOD THEREOF AND INDWELLING METHOD THEREOF

BACKGROUND OF THE INVENTION

1. Field of the Invention

The present invention relates to a stent, a manufacturing method thereof and indwelling method thereof, the stent being capable of opening intracorporeal lacuna for a long time for treatment of stricture of blood-vascular and non-blood-vascular system such as bile duct and digestive tract, and obstructive lesion, which has attracted attention in the field of so-called IVR (Interventional Radiology) treatment.

2. Description of Related Art

Broadly speaking, metal stents are classified into two types: one is set around a balloon catheter to be expanded and indwelled by balloon expansion; the other has expansibility by itself such as Z-stent and "wall-stent". Stainless steel, shape memory alloy or the like are used as material of the stent.

In order to indwell a stent having expansibility by itself, the stent such as the Z-stent is pushed out of a catheter to be released and indwelled, or a stent is set around a catheter-shaped core and covered with a sheath and is released when the sheath portion is drawn backward.

However, since the position of such stents cannot be corrected once expanded in the intracorporeal lacuna, additional stents are generally indwelled, which makes treatment difficult, increases burden on patients and deteriorates safety of the treatment.

In view of the above, a stent using bidirectional shape memory alloy is known (Japanese Patent Publication Hei 3-51430).

The stent uses bidirectional shape memory alloy wire composed of Ni—Ti type, Cu—Al—Ni type and Cu—Zn—Al type alloy formed in a shape capable of expanding and contracting in the diametral direction thereof, more specifically, a spiral shape, a spiral cylindrical shape, a cylindrically braided shape, or a pipe shape. The stent keeps a form expanded in diametral direction thereof at or around body temperature (35° C. to 37° C., for example) and becomes a form contracts in the diametral direction at a temperature substantially lower than body temperature (15° C. to 20° C., for example).

However, though the diameter of the stent using the bidirectional shape memory alloy expands and contracts in accordance with temperature change, the diameter change is small.

According to the description in the above Japanese '340 publication, the stent having a Ni—Ti type bidirectional shape memory alloy (containing approximately 51 atomic weight % of Ni) of 0.04 mm thick and 1 mm width has an inner diameter of approximately 2.0 mm at body temperature and contracts to approximately 1.4 mm of inner diameter at a temperature of not more than 15° C., exhibiting only approximately 0.6 mm of difference.

Accordingly, the stent cannot be indwelled into the intracorporeal lacuna and cannot be moved while firmly wound around a catheter.

Further, the stent disclosed in the Japanese Publication is not suited for practical use.

In other words, when deformation in two directions occurs, desired deformation cannot be securely obtained unless the material is suitably selected and thermal treatment is appropriately conducted, which results in difficulty in accurately controlling the shape and generated force.

Accordingly, the above-described stent using the bidirectional shape memory alloy has not been made into practical use at present.

SUMMARY OF THE INVENTION

To solve the above-described problems, an object of the present invention is to provide a stent and manufacturing method and indwelling method thereof, the stent capable of increasing change of diameter etc. enlarging and contracting in accordance with temperature change and capable of being configured into any shape at higher temperature and lower temperature, the stent therefore being suitably selected and used in different intracorporeal lacuna diameter, so that indwelling to the intracorporeal lacuna and position correction after indwelling can be facilitated to enhance safety and reduce burden for the patient.

In order to achieve the above object, a stent according to the present invention is arranged as follows.

A stent according to the present invention has a hollow cylindrical body made of a plurality of filament bodies of Ti—Ni alloy having excessive Ni, the hollow cylindrical body memorizing a first ashape during a lower-temperature shape memorizing process and a second shape during a higher-temperature shape memorizing process and being deformable between the first shape and the second shape in accordance with temperature change.

In other words, the stent is formed into the hollow cylindrical body by braiding the plurality of filament bodies, where the hollow cylindrical body is deformable into mutually different first and second shape. The lower-temperature shape memorizing process is conducted in the first shape condition and the higher-temperature shape memorizing process is conducted in the second shape, so that reversible deformation is possible between the two shapes in accordance with temperature change, in which the hollow body approaches the first shape in lower temperature and approaches the second shape in higher temperature.

The deforming shape may be any shape between the first shape and the second shape. In other words, between the first shape and the second shape, reversible deformation within an area from a shape similar to the first shape and slightly close to the second shape to a shape similar to the second shape and slightly close to the first shape, may also be possible.

The Ti—Ni alloy includes at least Ti and Ni. However, other chemical elements may be contained therein.

According to the present invention, since the hollow cylindrical body formed by braiding the plurality of filament bodies of Ni—Ti-alloy having excessive Ni experiences the lower-temperature shape memorizing process in the first shape and the higher-temperature shape memorizing process in the second shape to memorize both shapes, the hollow cylindrical body can change the shape thereof from the first shape to the second shape or from the second shape to the first shape, in accordance with temperature change.

Therefore, when the first shape and the second shape are set to have a smaller diameter in lower-temperature and a larger diameter in higher-temperature to secure enough difference between respective cylinder diameter, the diameters change enlarging and contracting in accordance with temperature change can be increased relative to the conventional stent and the enlarged and contracted shapes can be formed in any desired shape.

Further, the first shape and the second shape can be set in any configuration. For instance, the change in accordance with temperature may not be a change in diametral dimension but may be a change in axial dimension. For instance, the first shape may be linear tube and the second shape may be curved or bent cylindrical shape such as J-shape, L-shape, C-shape, U-shape and S-shape.

Further, the hollow cylindrical may not be a consecutive cylinder having constant diameter, but either the first shape or the second shape may be a tapered tube shape having a gradually changing diameter dimension. As described below, only the end portion of the cylinder may be enlarged in tapered manner.

In the stent according to the present invention, the lower-temperature shape memorizing process may preferably be a solution thermal treatment and the higher-temperature shape memorizing process may preferably be a constraint aging thermal treatment.

Accordingly, the shape memorization in the first shape and the second shape can be further securely conducted, thereby accurately controlling the respective shapes and generated force for increasing change between respective shapes.

In the stent according to the present invention, the first shape preferably has smaller cylinder diameter than the second shape.

According to the above, the stent can substitute for the above-described conventional stent. Since the diametral change in accordance with temperature change can be increased relative to the conventional stent, the stent can be freely selected and applied to intracorporeal lacuna having different diameter, so that indwelling to the intracorporeal lacuna and correction of the indwelled position can be easily conducted, thereby improving patient safety and reducing burden of the.

In the stent according to the present invention, crossed portions of the filament bodies may preferably be fixed only at both ends of the hollow cylindrical body.

Accordingly, since the crossed portions of the filament bodies are fixed on both ends of the hollow cylindrical body and the crossed portions of the other than both of ends are set free, the change in longitudinal direction can be reduced even when the diameter of the hollow cylindrical body is enlarged and contracted in accordance with temperature change. In other words, since the crossed portions of the filament bodies are fixed only on both ends of the hollow cylindrical body, the longitudinal change can be reduced while allowing a large diameter change (enlarging and contracting) in accordance with temperature change, thereby reducing indwelling error in indwelling the stent into the intracorporeal lacuna.

In the stent according to the present invention, the first shape of the hollow cylindrical body may preferably have a smaller diameter than the second shape and the second shape may preferably have a larger diameter at both opening ends than an intermediate portion thereof.

In conventional stents, after being inserted in the intracorporeal lacuna in a small-diameter condition of a lower-temperature, the stent is deformed with large-diameter condition a higher-temperature. In the deformation, though desired diameter enlargement can be obtained at the intermediate portion, it is known by experience that sufficient diameter enlargement cannot be obtained at both opening ends, which may cause disadvantage of humor flow toward the outer circumference of the stent and generation of thrombus etc. at that time.

On other hand, when the both opening ends are enlarged to have a larger diameter than the intermediate portion with enlarged condition, both opening ends enlarge to the same diameter as the intermediate portion or larger, thereby preventing humor flow into the outer circumference of the stent. Further, since the end portion of the stent firmly catches the wall of intracorporeal lacuna, unnecessary movement of the stent can be prevented.

In the stent according to the present invention, one or more of the plurality of filament bodies may preferably be made of gold or tantalum.

Accordingly, since the hollow cylindrical body includes the filament body of gold or tantalum photographable under fluoroscopy of roentgen rays, shadowing effect by X-rays can be expected, so that the position of the stent can be checked by roentgen rays when the stent is indwelled or withdrawn from the body. Accordingly, safe operation can be secured.

In the stent according to the present invention, the Ti—Ni alloy may preferably contain Co or Cu.

Accordingly, transformation temperature and deformation rate can be changed by the added elements, thereby being capable of selectively producing an expansive soft stent or an expansive rigid stent in accordance with usage.

Manufacturing methods of the stent according to the present invention includes the following arrangement.

A manufacturing method of a stent according to the present invention includes the steps of: braiding a plurality of filament bodies of Ti—Ni alloy of excessive Ni to form a hollow cylindrical body deformable into mutually different first and second shape; memorizing a lower-temperature shape for memorizing the first shape to the hollow cylindrical body as a lower-temperature shape; and memorizing a higher-temperature shape for memorizing the second shape to the hollow cylindrical body as a higher-temperature shape.

Accordingly, the first shape as the lower-temperature shape can be memorized to the hollow cylindrical body during the lower-temperature shape memorizing process and the second shape as the higher-temperature shape can be memorized during the higher-temperature shape memorizing process. Therefore, the first shape and the second shape can be securely memorized, thereby increasing shape change, enlargement and contraction for example, in accordance with temperature change and changing the hollow cylindrical body into any desired shape. Accordingly, the stent can be selectively freely applied to the intracorporeal lacuna having different diameter, thereby facilitating indwelling into the body and corrected at the indwelled position, so that patient safety can be improved and patients discomfort reduced.

In the manufacturing method of the stent according to the present invention, a solution thermal treatment may preferably be conducted during the lower-temperature shape memorizing step while keeping the hollow cylindrical body in the first shape, and an aging thermal treatment may preferably be conducted during the higher-temperature shape memorizing step while binding the hollow cylindrical body in the second shape.

According to the above arrangement, shape memorization of the first shape and the second shape can be further securely conducted, so that respective shapes and generated force can be accurately controlled and the change between the respective shapes can be further magnified.

An indwelling method of a stent according to the present invention includes the following steps.

An indwelling method of a stent according to the present invention includes the steps of: providing a stent having a first shape of lower-temperature with a larger the cylinder diameter than cylindrical diameter of a second shape of higher-temperature; accommodating the stent into a sheath after making it thinner than the cylinder diameter of the first shape; inserting a distal end of the sheath adjacent to the indwelling position of intracorporeal lacuna; and inserting a rod into the sheath and pushing out the stent in the sheath to indwell the stent in the intracorporeal lacuna.

Accordingly, since the diameter change enlarging and contracting in accordance with temperature change of the stent itself is large and the stent has approximately one ninth of the elastic modulus relative to stainless steel in martensitic structure, the stent can be accommodated in a thin sheath after applying outside force to make the cylinder diameter thinner. Therefore, the treatment can be facilitated as compared to a method in which the stent is held on an outside of distal portion of the catheter to be inserted into the intracorporeal lacuna.

BRIEF DESCRIPTION OF THE DRAWINGS

FIG. 12 is an illustration showing other embodiment of the stent according to the present invention; and FIGS. 13(A) and 13(B) are illustrations showing first and second shape of still other embodiment of the stent according to the present invention.

DETAILED DESCRIPTION OF PREFERRED EMBODIMENT(S)

An embodiment of the present invention will be described below with reference to attached drawings.

[Structure of Stent]

Figure 1:
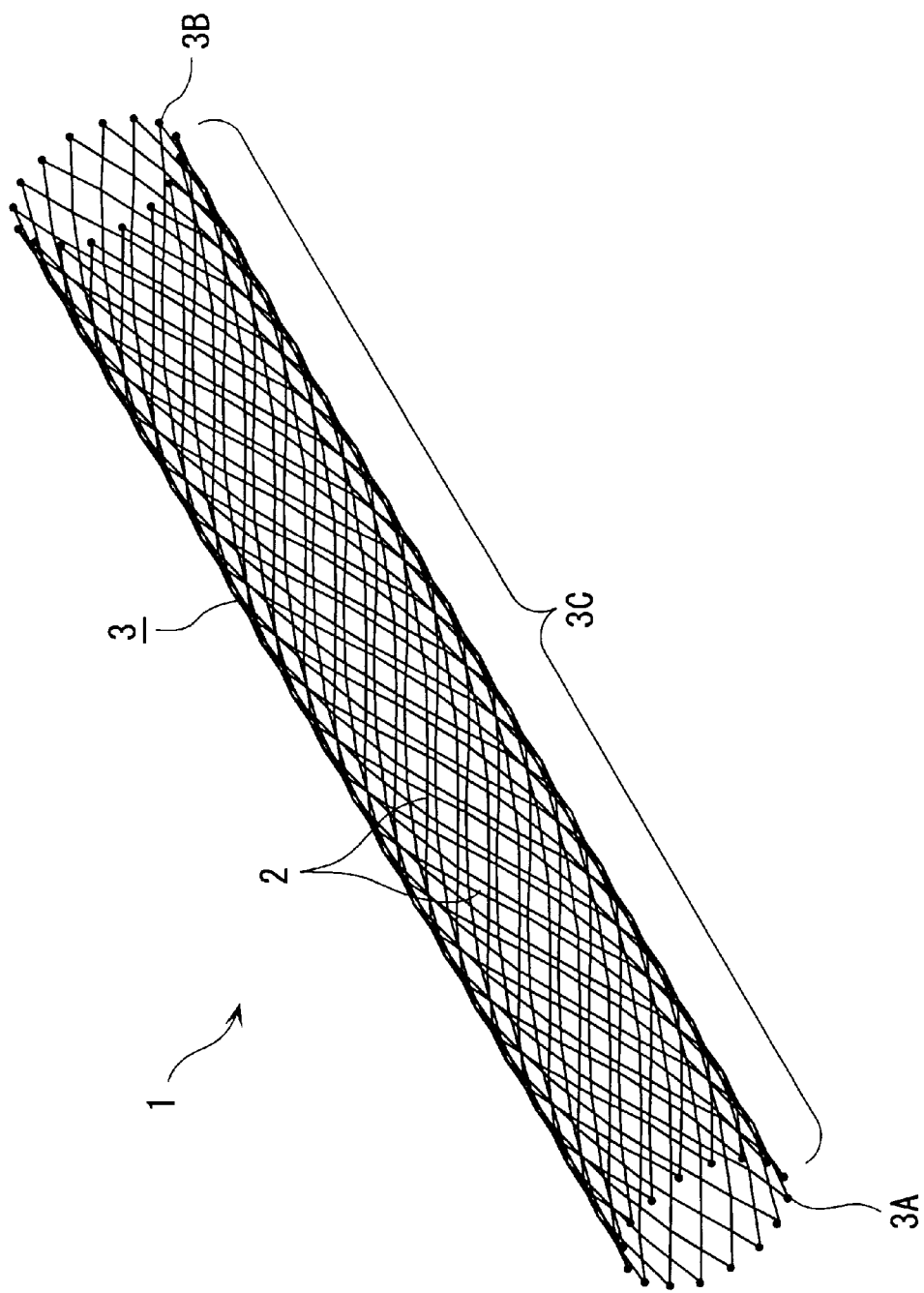
FIG. 1 is a perspective view showing an embodiment of the stent according to the present invention.

FIG. 1 is an outside perspective view of a stent 1 according to the present embodiment. The stent 1 is formed into a hollow cylindrical body 3 by braiding a plurality of filament bodies 2 of Ti—Ni alloy containing excessive Ni. Lower and higher temperature shape memorizing processes are respectively conducted on the hollow cylindrical body 3 while varying the diameter of the cylinder, so that a first shape (lower temperature shape) and a second shape (higher temperature shape) with different cylinder diameters are memorized and the cylinder diameter changes in accordance with temperature change.

The filament body 2 may be wire of Ti—Ni—Co alloy and Ti—Ni—Cu alloy as well as the Ti—Ni alloy or band-shaped body composed of the same. In this case, Ni content may preferably be not less than 50.5 wt %, more preferably, 54.0 to 56.5 wt %.

The thickness and number of filament bodies 2 can be determined considering hardness and flexibility of the stent 1 required in accordance with an indwelled portion of the stent. However, the number may preferably be a multiple of four, specifically, eight, sixteen and thirty-two and the like. For example, using twelve Ti—Ni wires and four tantalum wires (photographable under fluoroscopy of roentgen rays), the filament body 2 may be formed into the hollow cylindrical body 3 by alternately crossing (braiding) respective filament bodies 2 up and down. In this case, by braiding the respective filament bodies 2 so that the crossing angle of the respective filament body 2 becomes around 120 degrees, pressure endurance of the stent 1 can further be enhanced.

Only the crossed portions of the filament body 2 of the hollow cylindrical body 3 are fixed at both ends, and the crossed portions of the filament body 2 other than the portion except for both ends of the hollow cylindrical body 3 are in free condition.

More specifically, the crossed portions of sixteen filament bodies 2 are fixed at both ends 3A and 3B of the hollow cylindrical body 3 by welding etc., and the crossed portion of the filament bodies 2 at an intermediate portion 3C are kept being braided (touching with each other while crossing at a predetermined crossing angle). In other words, since the filament bodies 2 are mutually touching while being capable of freely changing crossing angle therebetween at the intermediate portion 3C of the hollow cylindrical body 3 except for the both ends 3A and 3B, the diameter change in accordance with temperature change can be increased.

Figure 2:
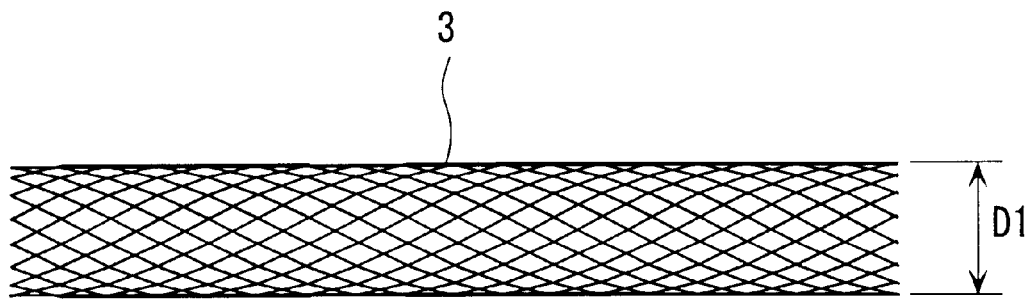
FIG. 2 is a front elevation showing the stent changed into lower temperature shape (contracted)
Figure 3:
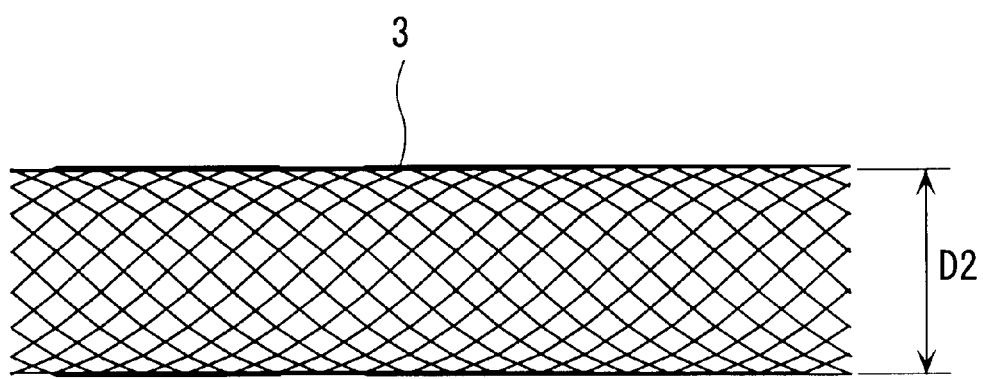
FIG. 3 is a front elevation showing the stent changed into higher temperature shape (expanded)

Further, the hollow cylindrical body 3 memorizes the lower-temperature shape and the higher-temperature shape having different cylindrical diameters by the lower-temperature shape memorizing process and the higher-temperature shape memorizing process while changing the cylinder diameter. In other words, at lower temperature, when the temperature of the hollow cylindrical body 3 is lower than the body temperature, for example, the hollow cylindrical body 3 is shape-memorizing processed, so that the diameter becomes first diameter D1 as shown at FIG. 2. On the contrary, in higher temperature, when the temperature of the hollow cylindrical body 3 is around the body temperature higher than the first temperature, for example, the diameter changes into second diameter D2 larger than the first diameter D1 as shown in FIG. 3.

Specifically, in the example of a dog abdominal aorta, when the temperature of the hollow cylindrical body 3 is around 15° C. (approximately 12° C. to 18° C.), the diameter of the hollow cylindrical body 3 becomes approximately 5 to 8 mm. When the temperature of the hollow cylindrical body 3 is approximately 34° C. to 37° C., the diameter of the hollow cylindrical body 3 becomes approximately 12 to 16 mm. Under an environment of temperature of 5° C. to 10° C., since the hollow cylindrical body is a martensitic structure and has an elastic modulus of one ninth of stainless steel, which is relatively soft, the cylinder diameter can be further reduced to around 2 mm when an outside force is applied to narrow the hollow cylindrical body 3.

[Manufacturing Method of Stent]

The manufacturing method of the stent includes following steps.

1) Braiding step for forming the hollow cylindrical body 3 by braiding a plurality of filament bodies 2 made of Ti—Ni alloy having excessive Ni.
2) Fixing step for fixing crossed portions of the filament body 2 at both ends of the hollow cylindrical body 3.
3) Lower-temperature shape memorizing process for conducting solution thermal treatment on the hollow cylindrical body 3 to memorize the lower-temperature shape.
4) Higher-temperature shape memorizing process for conducting constraint aging thermal treatment while binding the hollow cylindrical body 3 in a cylinder diameter different from the lower-temperature shape to memorize the higher-temperature shape.

In the braiding step, a plurality of filament bodies 2 (sixteen Ti—Ni wires or twelve Ti—Ni wires and four tantalum wires) are wound around a cored bar of 20 mm diameter and are braided (plaiting respective filament body 2 alternately crossing up and down) to form the hollow cylindrical body 3. Incidentally, the thickness, number and braid pitch may be appropriately selected in accordance with the intracorporeal lacuna to be applied with the stent.

Figure 4:
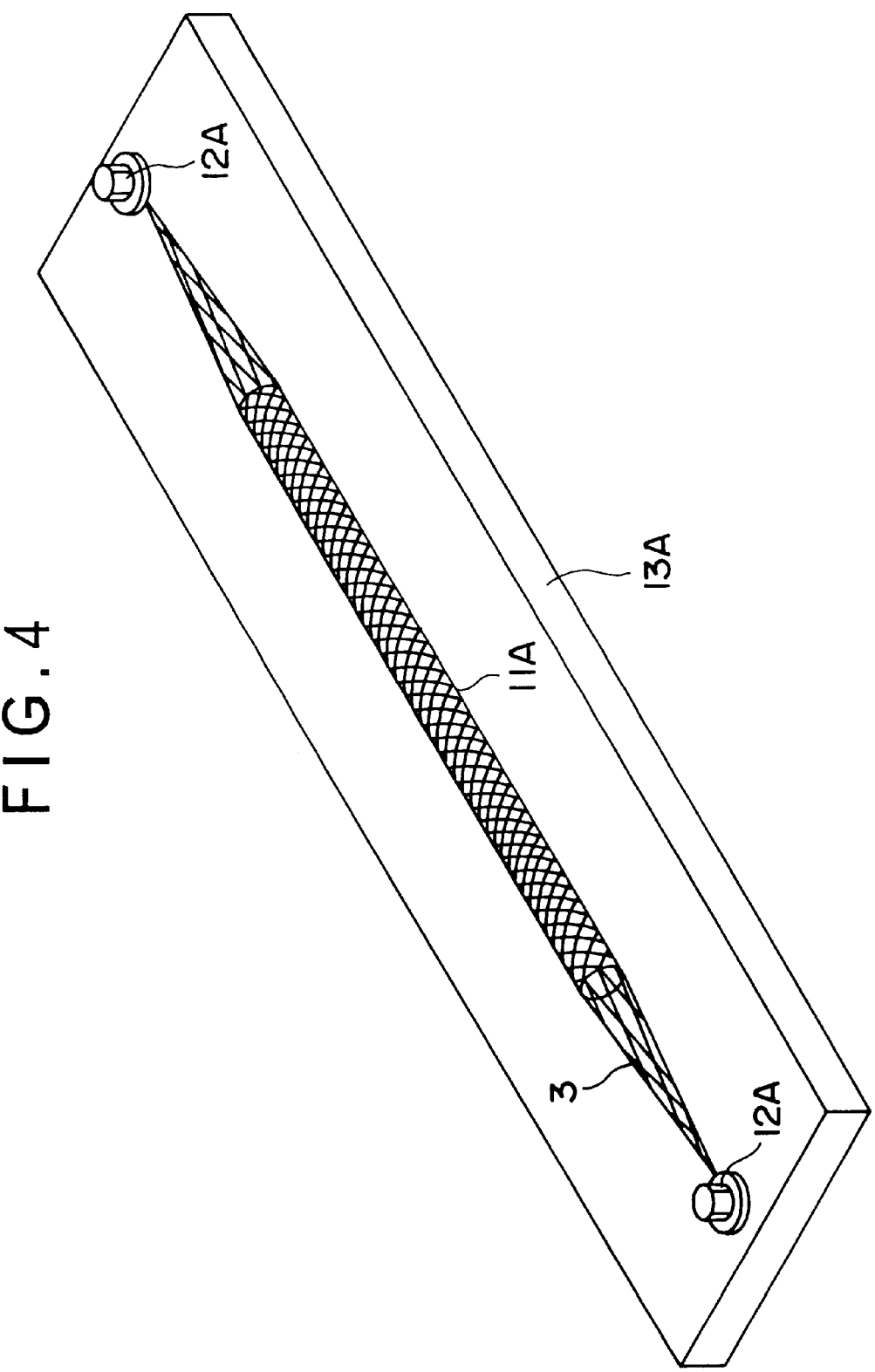
FIG. 4 is a perspective view showing constraint condition of hollow cylindrical body in lower temperature shape memorizing process of the stent.

In the lower-temperature shape memorizing process, the hollow cylindrical body 3 is inserted into a cored bar (stainless steel bar) 11A having diameter of, for example, 2 mm as shown in FIG. 4, the hollow cylindrical body 3 is restricted to the cored bar 11A by narrowing inner diameter thereof by stretching both ends, and the both ends are firmly fixed to a steel plate 13A with a screw 12A.

The lower-temperature shape memorizing process is conducted under the above condition. During the lower-temperature shape memorizing process, solution thermal treatment is conducted to the hollow cylindrical body 3 under FIG. 4 condition at a temperature of more than 600° C. More specifically, the hollow cylindrical body 3 is heated for approximately one hour at a temperature around 700° C. to 1000° C. and is cooled subsequently.

In the fixing step, the hollow cylindrical body 3 having experienced with lower-temperature shape memorizing process is inserted to a cored bar having diameter of, for example, 11 mm. While both ends of the hollow cylindrical body 3 is stretched to restrict to the cored bar (i.e. enlarging larger 1 than the first diameter D1), the crossed portions of the filament bodies 2 are welded on the both ends.

More specifically, the hollow cylindrical body 3 is wound around an electrode of a welding machine (an electrode having a diameter of approximately 11 mm), and the crossed portions of the filament body 2 on both ends are welded in this condition.

Figure 5:
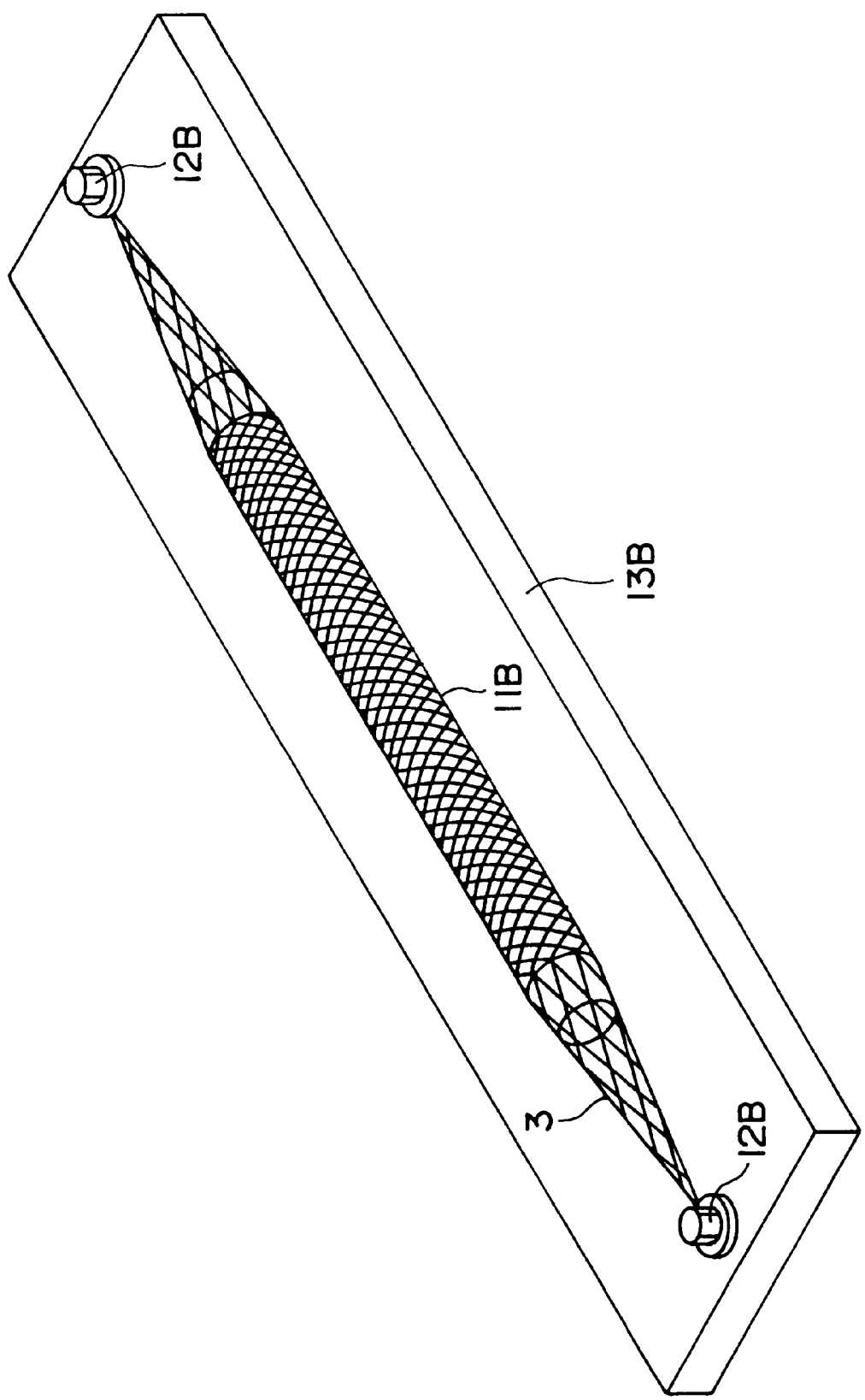
FIG. 5 is a perspective view showing constraint condition of hollow cylindrical body in higher temperature shape memorizing process of the stent.

In the higher-temperature shape memorizing process, the hollow cylindrical body 3 having experienced the fixing step is inserted to a cored bar having a diameter of, for example, 15 mm as shown in FIG. 5, and both ends thereof are stretched so that the hollow cylindrical body 3 is restricted to the cored bar 11B and the both ends are firmly fixed to a steel plate 13B by a screw 12B.

The higher-temperature shape memorizing process is conducted under the above condition. During the higher-temperature shape memorizing step, constraint aging thermal treatment is conducted on the hollow cylindrical body 3. More specifically, the hollow cylindrical body 3 is heated at a temperature of approximately 300° C. to 560° C. for about one hour and is cooled subsequently.

Figure 6:
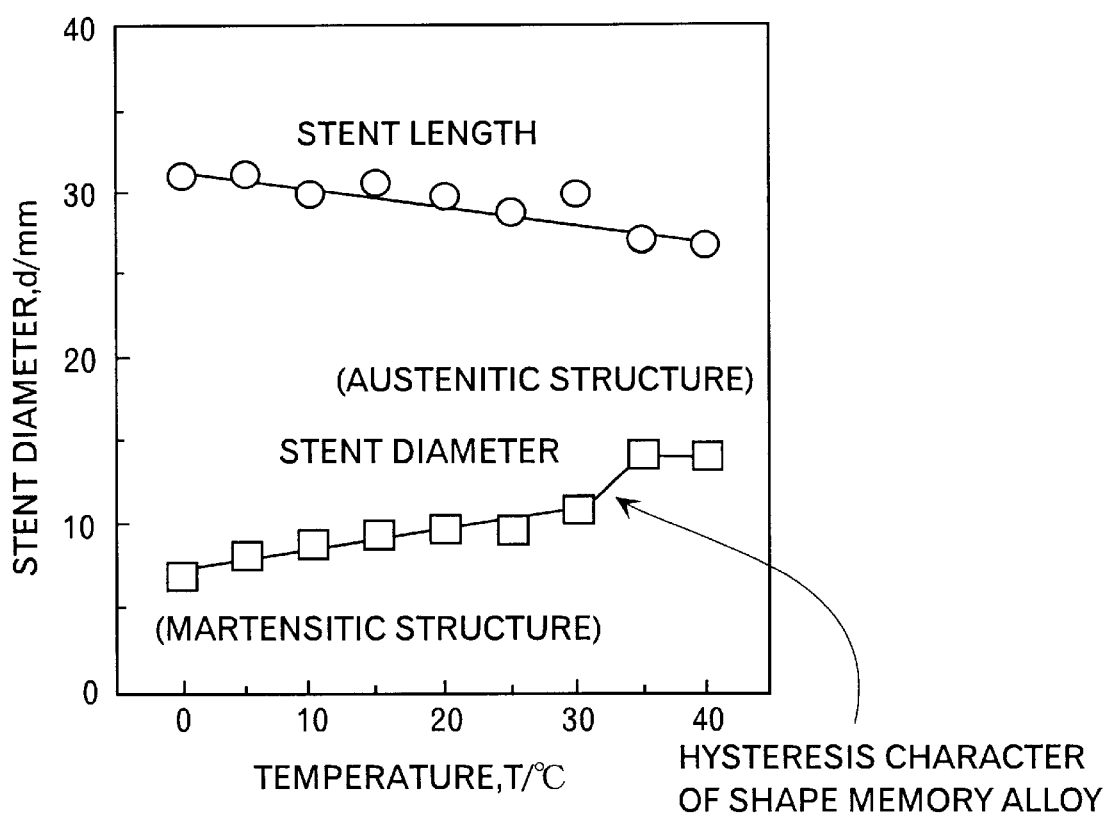
FIG. 6 is a graph showing diameter and length change in accordance with temperature change of the stent.

Consequently, as shown in FIG. 6, the stent 1 is obtained, in which the diameter of the hollow cylindrical body 3 is around 8 mm when the temperature of the hollow cylindrical body 3 is approximately 15° C. and the diameter of the hollow cylindrical body 3 changes to around 14 mm when the temperature of the hollow cylindrical body 3 becomes approximately 34° C. to 37° C. Further, as can be seen from FIG. 6, the length of change the stent 1 is small (the length changes approximately 4 mm).

[Using Method of Stent]

Figure 7:
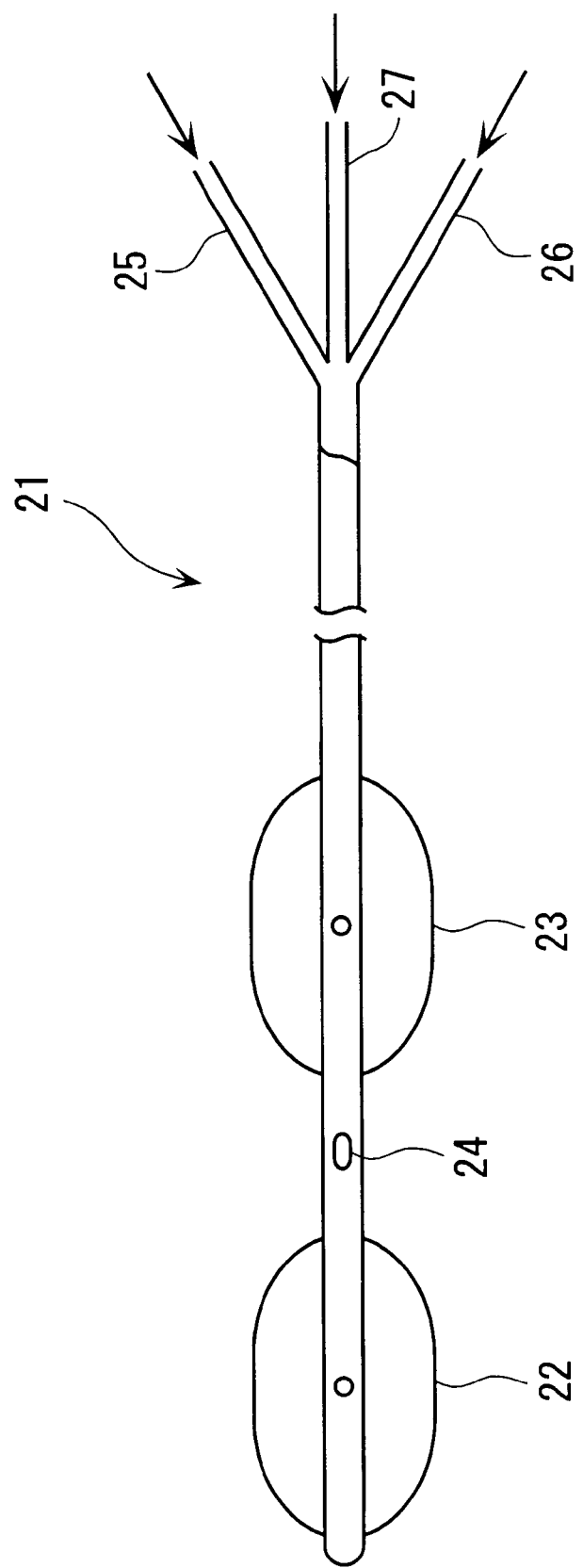
FIG. 7 is an illustration of balloon catheter used for indwelling the stent into body.

In order to indwell the stent 1 to a target position of the intracorporeal lacuna, a balloon catheter 21 shown in FIG. 7 is used.

A bloodstream shut balloon 22 and a stent moving balloon 23 are provided spaced apart at a predetermined interval at a distal portion thereof and a flush hole 24 is formed therebetween. The bloodstream shut balloon 22 and the stent moving balloon 23 are expanded by fluid supplied from branch induction tubes 25 and 26. Cold physiological saline or warm physiological saline supplied from a branch induction tube 27 is discharged from the flush hole 24.

When the stent 1 is indwelled, the stent 1 is inserted to a distal position of the catheter 21 (a position corresponding to the stent moving balloon 23) as shown in FIG. 8 and the cold physiological saline is discharged from the flush hole 24 of the catheter 21. Then, the stent 1 is cooled and contracted by the cold physiological saline from the flush hole 24 and is firmly touched on the distal portion of the catheter 21 through the stent moving balloon 23 (see FIG. 8(A)).

Figure 8A:
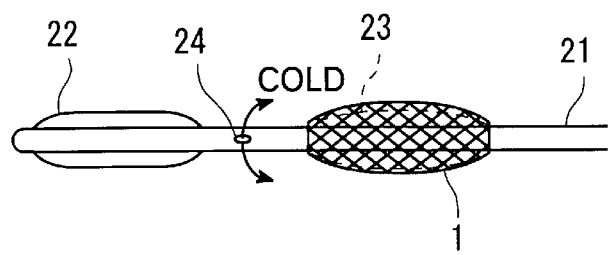
FIG. 8(A) to FIG. 8(E) are illustrations showing process for indwelling the stent using the balloon catheter.
Figure 8B:
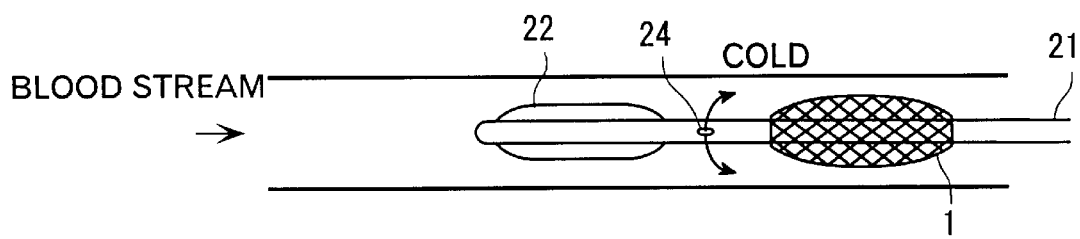
Figure 8C:
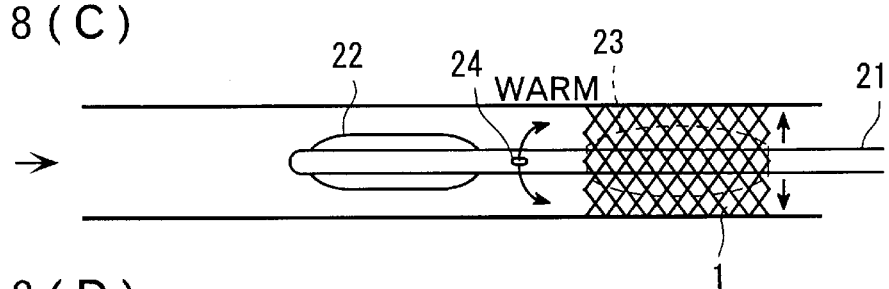
Figure 8D:
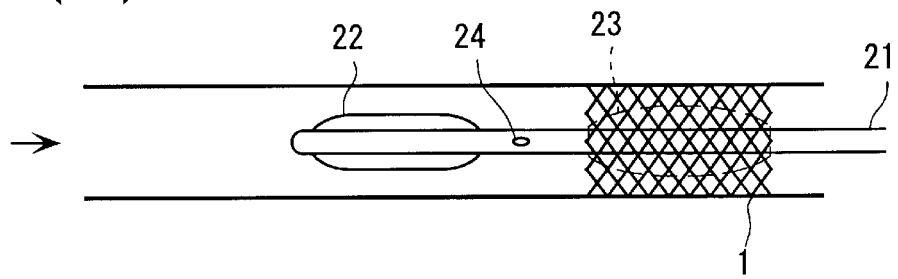
Figure 8E:
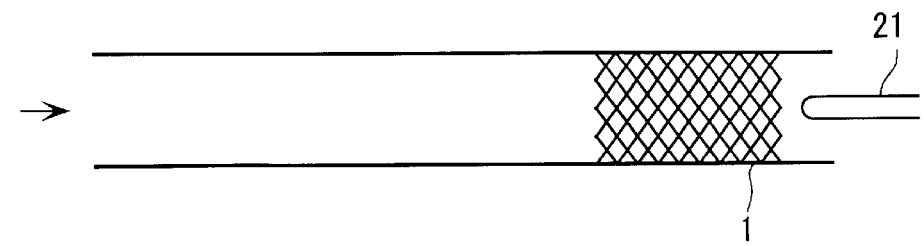

While maintaining the above condition, the stent 1 is introduced to a target indwelling position by virtue of guide wire introduced in the intracorporeal lacuna beforehand (see FIG. 8(B)), and subsequently, the discharge of the cold physiological saline is suspended and warm physiological saline is discharged (see FIG. 8(C)). Then, the stent 1 is rapidly warmed by the warm physiological saline and is retained on an inner wall of the intracorporeal lacuna while being expanded. Under this condition, since the stent 1 is warmed by body temperature, the stent is retained under the diameter when the discharge of the warm physiological saline is suspended (see FIG. 8(D)). Thereafter, the catheter 21 is pulled out (see FIG. 8(E)).

Figure 9A:
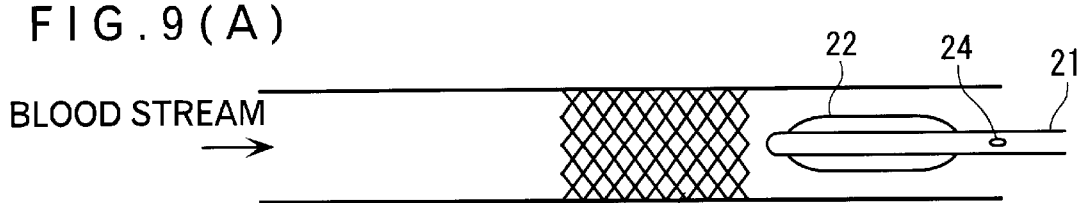
FIG. 9(A) to FIG. 9(G) are illustrations showing process for correcting indwelling position of the stent using the balloon catheter.

On the other hand, as shown in FIG. 9, when the stent 1 is to be withdrawn or the indwelling position thereof is to be moved, the distal portion of the catheter 21 is inserted through an inside of the stent 1 (see FIG. 9(A)) to a position where the stent moving balloon 23 corresponds to the stent 1.

Figure 9B:
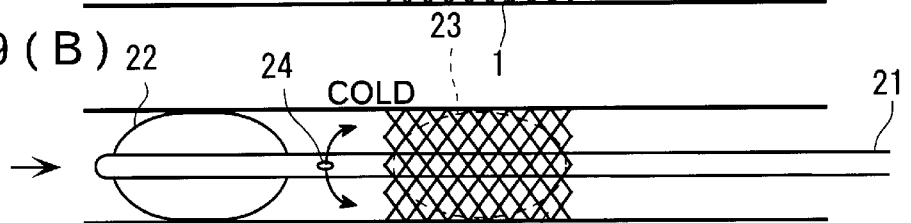
Figure 9C:
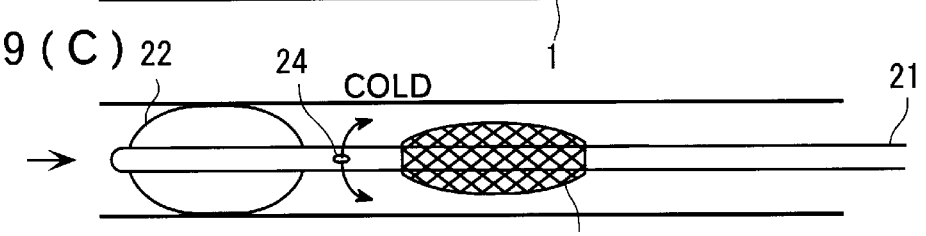

At this position, the bloodstream shut balloon 22 and the stent moving balloon 23 are expanded and cold physiological saline is discharged from the flush hole 24 of the catheter 21 (see FIG. 9(B)). Then, since the stent 1 is cooled and contracted, the stent 1 is held on the distal portion of the catheter 21 through the stent moving balloon 23 (see FIG. 9(C)).

Figure 9D:
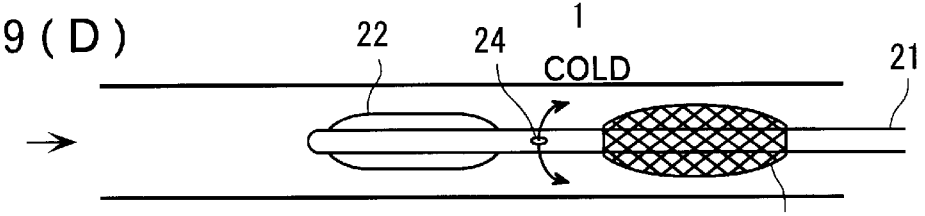
Figure 9E:
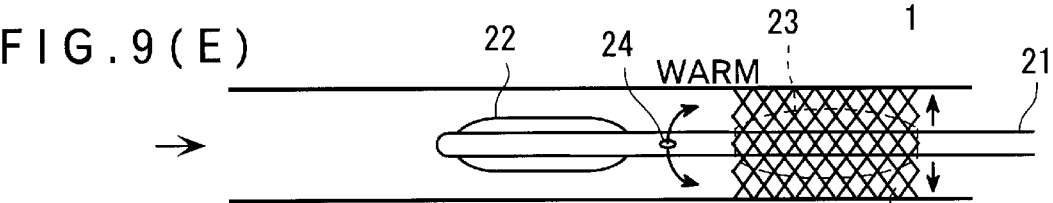
Figure 9F:
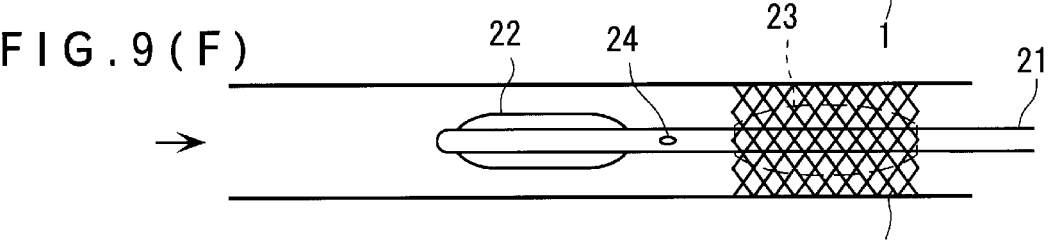
Figure 9G:
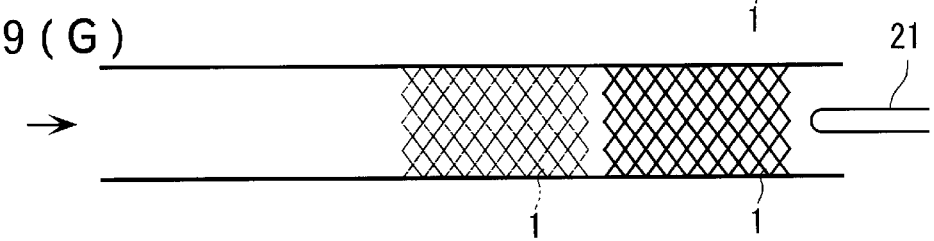

Subsequently, while the bloodstream shut balloon 22 is contracted after the stent 1 is moved to a new indwelling position (see FIG. 9(D)), the warm physiological saline is discharged from the flush hole 24 of the catheter 21 (see FIG. 9(E)). Then, the stent 1 is rapidly warmed and expanded by the warm physiological saline, the stent 1 is held on the inner wall at the indwelling position (see FIG. 9(F)). Since the stent 1 is warmed by the body temperature and the diameter is maintained when the discharge of the warm physiological saline is suspended, the catheter 21 can be pulled out from the intracorporeal lacuna (see FIG. 9(G)).

Incidentally, the scope of the present invention is not limited to the aforesaid embodiment but includes other embodiment and modifications.

In the aforesaid embodiment, the stent 1 is indwelled in the body, moved from the indwelled position and withdrawn from the body using the balloon catheter having two balloons 22 and 23 at a distal portion thereof. However, the stent 1 can be indwelled in the body by other method.

Figure 10A:
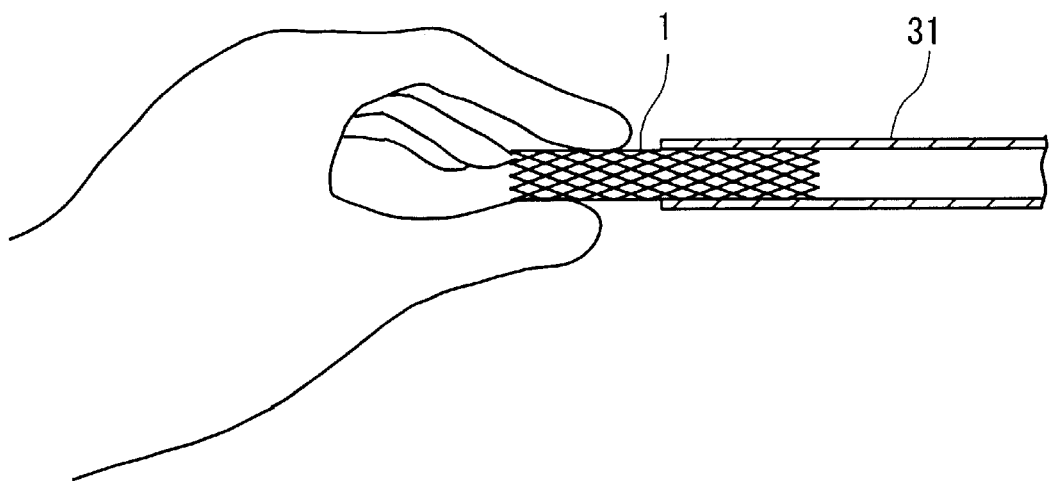
FIGS. 10(A) and 10(B) are illustrations showing how the stent is indwelled in the body using a sheath.
Figure 10B:
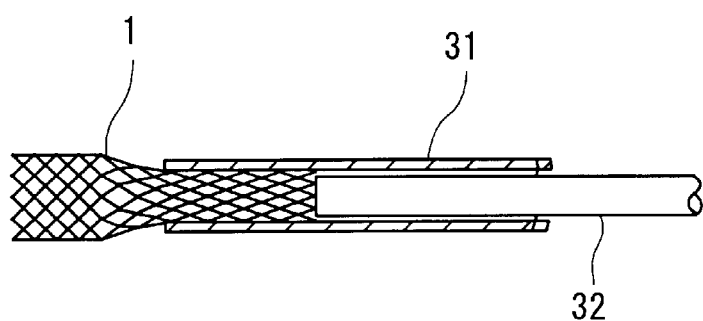

For instance, as shown in FIG. 10, the stent 1 may be picked by fingers to make the stent thinner than the cylinder diameter of the lower-temperature shape to accommodate in a sheath 31 (see FIG. 10(A)). After a distal end of the sheath 31 is inserted adjacent to indwelling position in the intracorporeal lacuna, a pushing rod 32 may be inserted into the sheath 31 to push out the stent 1 in the sheath 31 (see FIG. 10(B)) to indwell the stent 1 in the intracorporeal lacuna.

Accordingly, since the diameter itself of the stent 1 largely changes in accordance with temperature change and elastic modulus thereof is one ninth of stainless steel (meaning soft) in martensitic structure, the cylinder diameter can be further reduced by applying outside force to narrow the diameter, so that the stent 1 can be accommodated in the thin sheath 31. Accordingly, the stent 1 can be indwelled in the intracorporeal lacuna while reducing the burden on the patients, thereby more easily and safely conducting treatment than, for instance, a method for retaining the stent on a distal outside of the catheter to insert into the intracorporeal lacuna.

Further, the position of the stent 1 can be corrected according to a method other than the method described in the aforesaid embodiment.

Figure 11A:
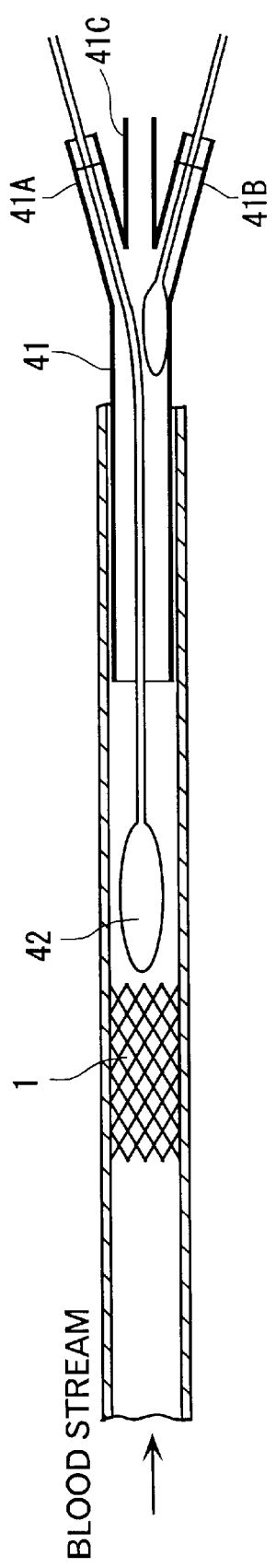
FIG. 11(A) to FIG. 11(C) are illustrations showing other example for correcting the position of the stent.
Figure 11B:
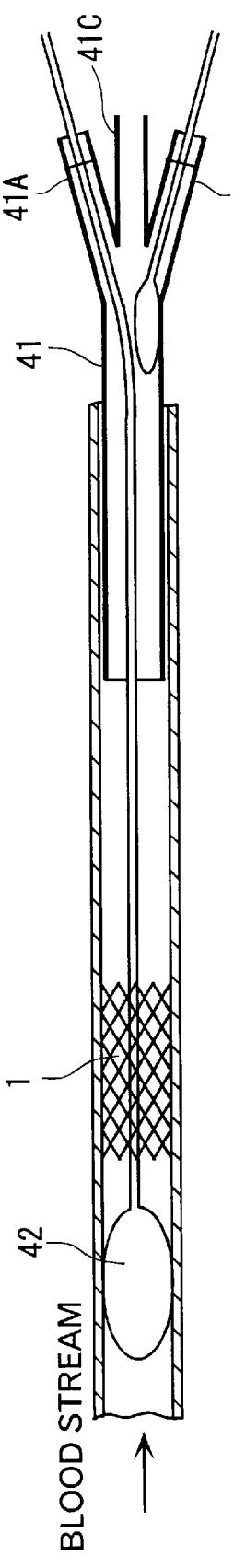
Figure 11C:
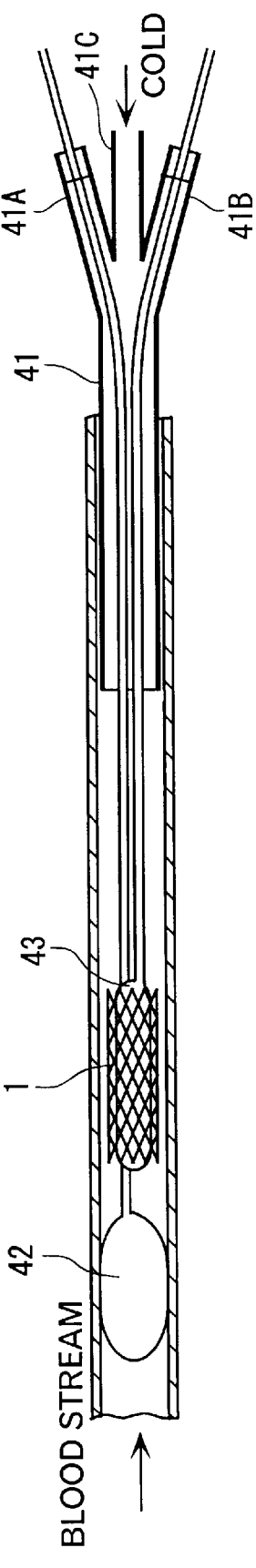

For instance, as shown in FIG. 11, after inserting a sheath 41 having a check-valve-attached balloon inserts 41A and 41B and cold physiological saline inlet 41C at a base end thereof, first balloon catheter 42 is inserted from the balloon insert 41A (see FIG. 11(A)).

After further advancing the first balloon catheter 42 to be located in front of the stent 1 relative to the bloodstream, the first balloon catheter 42 is expanded at the position (see FIG. 11(B)).

Subsequently, after inserting second balloon catheter 43 from the balloon inlet 41B to be located in the stent 1, the cold physiological saline is injected from the cold physiological saline inlet 41C. Then, the stent 1 is cooled and contracted and is touched and held by the second balloon 43 (see FIG. 11(B)). When the first balloon catheter 42 is contracted from the condition, the stent 1 becomes movable, and is capable of moving at any position.

The stent itself can be modified as follows.

Though the cylinder diameter is changed between the lower-temperature shape memorizing process and the higher-temperature shape memorizing process so that the cylinder diameter in lower-temperature shape (first shape) is larger than the cylinder diameter in higher-temperature shape (second shape), the shape memorizing process may be conducted for establishing a reverse configuration. In other words, the shape memorizing process may be conducted changing the cylinder diameter between the lower-temperature shape memorizing process and the higher-temperature shape memorizing process so that the cylinder diameter of the higher-temperature shape is smaller than the cylinder diameter of the lower-temperature shape.

In the aforesaid embodiment, the cylinder diameter of the lower-temperature shape is constant cylinder diameter D1 from one opening end to the other opening end and the cylinder diameter of the higher-temperature shape is constant cylinder diameter D2. However, when the cylinder diameter D2 of higher-temperature is set larger than the cylinder diameter D1 of lower-temperature, sufficient enlargement of the diameter sometimes cannot be obtained at the opening end (i.e., the opening end is narrowed in approximately tapered shape when the diameter of the intermediate portion is enlarged to the cylinder diameter D2).

Such problem can be solved by setting the opening of both ends larger than the intermediate portion in the lower-temperature shape (first shape).

In the other embodiment shown in FIG. 12, the stent 1 is configured approximately the same as the embodiment of FIG. 1, where the hollow cylinder body 3 entirely has the cylinder diameter D1 in the lower-temperature shape as the first shape. However, in the higher-temperature shape as the second shape, though the intermediate portion thereof has cylinder diameter D2, the opening portions 3A and 3B of both ends are enlarged to be cylinder diameter D3.

According to the present embodiment, in addition to the same effect as described in the FIG. 1 to FIG. 10, the fluidity of humor is unlikely to be influenced in indwelling into the intracorporeal lacuna since the opening end is not narrowed in widening the diameter.

In the aforesaid embodiment, both of the lower-temperature shape (first shape) and the higher-temperature shape (second shape) of the stent 1 is linear tube with variable tube the tube diameter. However, the change between the respective shapes is not restricted to the change in tube diameter, and the changing shape is not restricted to the linear tube.

For instance, either the first shape in lower-temperature or the second shape in higher-temperature may be curved tube or bent L-shape.

In the still other embodiment shown in FIG. 13, the hollow cylindrical body 3 of the stent 1 has the first shape in lower-temperature with tube diameter D1 and straight axial line 3C as shown in FIG. 13(A). On the other hand, as shown in FIG. 13(B), though the tube diameter of the second shape in higher-temperature remains D1, the axial line 3C is curved in arc shape. Such stent 1 is in a linear shape in lower-temperature as shown in FIG. 13(A), which changes in a curved shape in higher-temperature as shown in FIG. 13(B).

According to such change, the stent 1 can be more appropriately applied to a curved intracorporeal lacuna, thereby allowing the humor or fluid substance passing through the intracorporeal lacuna to flow smoothly.

Incidentally, the tube diameter may be set variable accompanying the above-described deformation of the axial line.

When the tube diameter is changed, the diameter is not restricted to be uniformly enlarged on the entirety of the stent 1. In other words, diameter enlarging ratio may be set large on one end and diameter enlarging ratio may be set small on the other end, so that the second shape may be tapered-tube shape even with the first shape of tube shape of entirely the same diameter.

Though the fixing step for fixing the crossed portion of the filament body 2 at both ends of the hollow cylindrical body 3 is conducted after the lower-temperature shape memorizing process in the aforesaid embodiment, other arrangement is possible.

Specifically, the fixing step may be conducted prior to lower-temperature shape memorizing process or after higher-temperature shape memorizing process.

What is claimed is:

1. A stent comprising a hollow body made of a plurality of braided filament bodies of an iron-free Ti—Ni alloy having excessive Ni, the hollow body memorize a first shape during a lower-temperature shape memorizing process and a second shape during a higher-temperature shape memorizing process and being reversibly deformable between the fist shape and the second shape in accordance with temperature change;

wherein the lower-temperature shape memorizing process is a solution thermal treatment and the higher-temperature shape memorizing process is a constraint aging thermal treatment; and the solution thermal treatment is conducted at a temperature higher than about 800° C. and lower than or equal to about 1000° C.

2. The stent according to claim 1, wherein the first shape has a diameter smaller than that of the second shape.

3. The stent according to claim 2, wherein the braided filament bodies are fixed only at both ends of the hollow body.

4. The stent according to claim 2, wherein the diameter of the second shape is larger at both opening ends than in an intermediate portion thereof.

5. The stent according to claim 1, wherein one or more than one of the plurality of filament bodies is/are made of gold or tantalum.

6. The stent according to claim 1, wherein the Ti—Ni alloy further contains Co or Cu.

7. The stent of claim 1, wherein said hollow body is a hollow cylindrical body.

8. A method of manufacturing a stent, comprising the steps of:

braiding a plurality of filament bodies of an iron-free Ti—Ni alloy of excessive Ni to form a hollow body deformable into mutually different first and second shapes;

conducting a lower-temperature shape memorizing process for causing the hollow body to memorize the first shape as a lower-temperature shape; and conducting a higher-temperature shape memorizing process for causing the hollow body to memorize the second shape as a higher-temperature shape;

wherein a solution thermal treatment is conducted during the lower-temperature shape memorizing process and a constraint aging thermal treatment is conducted during the higher-temperature shape memorizing process; and the solution thermal treatment is conducted at a temperature higher than about 800° C. and lower than or equal to about 1000° C.

9. The method according to claim 8, wherein the solution thermal treatment is conducted while keeping the hollow body in the fist shape, and the constraint aging thermal treatment is conducted while binding the hollow body in the second shape.

10. The method of claim 8, wherein said hollow body is a hollow cylindrical body.

* * * * *